US011877981B2

(12) United States Patent
Hayes et al.

(10) Patent No.: US 11,877,981 B2
(45) Date of Patent: Jan. 23, 2024

(54) CONTAINER FOR PERSONAL HEALTH COMPOSITIONS

(71) Applicants: The Procter & Gamble Company, Cincinnati, OH (US); PolyOne Corporation, Avon Lake, OH (US)

(72) Inventors: Michael Devon Hayes, West Chester, OH (US); Leigh Mahoney, Liberty Township, OH (US); Lonnie Stuckert, Wilmington, OH (US); Greg Veintimilla, Maineville, OH (US); Gary Vernon, Sugar Hill, GA (US)

(73) Assignee: The Procter & Gamble Company, Cincinnati, OH (US)

( * ) Notice: Subject to any disclaimer, the term of this patent is extended or adjusted under 35 U.S.C. 154(b) by 659 days.

(21) Appl. No.: 16/704,287

(22) Filed: Dec. 5, 2019

(65) Prior Publication Data
US 2020/0179223 A1 Jun. 11, 2020

Related U.S. Application Data

(60) Provisional application No. 62/775,422, filed on Dec. 5, 2018.

(51) Int. Cl.
| *A61J 1/03* | (2023.01) |
| *B29C 49/00* | (2006.01) |
| *C09B 1/20* | (2006.01) |
| *A61K 9/08* | (2006.01) |
| *A61K 31/4045* | (2006.01) |

(52) U.S. Cl.
CPC ............. *A61J 1/03* (2013.01); *B29C 49/0005* (2013.01); *C09B 1/207* (2013.01); *A61J 2200/50* (2013.01); *A61K 9/08* (2013.01); *A61K 31/4045* (2013.01)

(58) Field of Classification Search
CPC ..... A61J 1/03; A61J 2200/50; B29C 49/0005; C09B 1/207; A61K 9/08; A61K 31/4045
USPC ........................................................ 206/528
See application file for complete search history.

(56) References Cited

U.S. PATENT DOCUMENTS

| 6,197,851 | B1 | 3/2001 | Maxwell |
| 6,355,723 | B1 | 3/2002 | Van |
| 9,314,489 | B2 | 4/2016 | Kelly |
| 9,486,487 | B2 | 11/2016 | Cutcliffe |
| 10,087,304 | B2 | 10/2018 | Zhu |
| 2006/0035924 | A1* | 2/2006 | Schmid .................. A61J 1/067 514/310 |
| 2007/0299127 | A1 | 12/2007 | Velazquez et al. |
| 2011/0168596 | A1 | 7/2011 | Fujita |
| 2012/0165422 | A1* | 6/2012 | Vernon ............... B29C 49/0005 524/502 |
| 2018/0140648 | A1 | 5/2018 | Segal |

FOREIGN PATENT DOCUMENTS

| ES | 2353865 T3 | 3/2011 |
| JP | 2002068202 A | 3/2002 |
| JP | 2003341748 A | 12/2003 |
| WO | WO2007129893 A1 | 11/2007 |
| WO | WO2011040905 A1 | 4/2011 |
| WO | WO2016058985 A1 | 4/2016 |
| WO | WO2016070151 A1 | 5/2016 |
| WO | 2018112036 A1 | 6/2018 |

OTHER PUBLICATIONS

Heredia-Guerrero et al. Cutin from agro-waste as a raw material for the production of bioplastics. Journal of Experimental Botany, vol. 68, No. 19 pp. 5401-5410, 2017. (Year: 2017).*
PCT Search Report and Written Opinion for PCT/US2019/064570 dated Mar. 10, 2020.

* cited by examiner

Primary Examiner — Yih-Horng Shiao
(74) Attorney, Agent, or Firm — Gregory S. Darley-Emerson; Amanda Herman Berghauer

(57) ABSTRACT

A container for personal health compositions with melatonin. The container has a polyester and a colorant composition with at least two dyes and a pigment. The container can filter out the wavelengths of visible light that contribute to the photodegradation of melatonin during storage in normal factory or home light conditions.

10 Claims, 3 Drawing Sheets

US 11,877,981 B2

CONTAINER FOR PERSONAL HEALTH COMPOSITIONS

The subject matter disclosed in this application was developed and the claimed invention was made by, or on behalf of, one or more parties to a joint research agreement that was in effect on or before the effective filing date of the claimed invention. The claimed invention was made as a result of activities undertaken within the scope of the joint research agreement. The parties to that joint research agreement are The Procter & Gamble Company and PolyOne Corporation. Therefore, subject matter disclosed herein and the claimed invention herein shall be deemed to have been owned by the same person or subject to an obligation of assignment to the same person in applying the provisions of subsection 35 USC § 102 (b)(2)(C).

FIELD OF THE INVENTION

The present invention is directed to containers for compositions, preferably personal health compositions, and methods of use thereof. The present invention is also directed a container that can mitigate the photodegradation of compositions stored within said container and methods of use thereof.

BACKGROUND OF THE INVENTION

Melatonin is a naturally occurring hormone produced by the pineal gland, which regulates wakefulness. A personal health composition comprising melatonin can be used to promote the onset of sleep. Unfortunately, melatonin can be prone to photodegradation under normal conditions experienced during manufacture, packaging, while on the shelf at a store, and/or when stored by a consumer prior to use. The photodegradation of melatonin can limit the effectiveness of the personal health composition.

Some strategies to mitigate the photodegradation of melatonin include using an opaque container, using a colored container, such as an amber container, or completely covering the container with removable packaging material. However, these strategies either prevent the consumer from visually inspecting the contents of the container to assess the quantity or quality of the personal health composition, are ineffective at preventing the photodegradation of melatonin, or are detrimental to the customer purchasing experience. Thus, there is a need for containers to store personal health compositions comprising melatonin that mitigate the photodegradation of melatonin. As such, the present invention is directed to containers that can mitigate the photodegradation of melatonin and methods of use thereof.

SUMMARY OF THE INVENTION

Disclosed herein is a product comprising a container comprising (i) a polyester, (ii) a colorant composition comprising (1) a first anthraquinone dye, (2) a second anthraquinone dye, and (3) titanium dioxide; and (b) a liquid composition comprising melatonin.

Also disclosed herein is a container for a composition, the container comprising (a) a polyester; (b) a colorant composition comprising (i) a first anthraquinone dye; (ii) a second anthraquinone dye absorbing visible light above 650 nm in an amount of at least 0.04 weight percent of the container; and (iii) titanium dioxide, wherein the container absorbs, reflects, and blocks light in the range of 190 nm-750 nm at 1% or less light transmission at a container thickness of 0.5 mm.

Also disclosed herein is a product comprising (a) a container comprising (i) a polyester, (ii) a colorant composition and (b) an aqueous composition comprising melatonin, wherein the composition has a percent loss of melatonin of about 30% or less, by weight of melatonin, after 100 days of exposure to normal factory or home light levels.

Also disclosed herein is a method of minimizing the photodegradation of melatonin in a liquid composition comprising (a) providing a container comprising (i) a polyester; (ii) a colorant composition comprising (1) a first anthraquinone dye; (2) a second anthraquinone dye absorbing visible light above 650 nm in an amount of at least 0.04 weight percent of the container; and (3) titanium dioxide; and (b) storing a liquid composition comprising melatonin in the container from manufacture of the composition until use by a consumer.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

The present invention is directed to containers for personal health compositions and methods of use thereof. Also, the present invention is directed to containers for personal health compositions comprising melatonin, which can be sensitive to photodegradation during the time after its initial manufacture. More particularly, the containers can comprise a colorant composition that can mitigate the photodegradation of melatonin.

Without wishing to be bound by theory, it is believed that when energy from electromagnetic radiation exceeds a compound's molecular bonding energy, photodegradation occurs. Additionally, when a compound is exposed to electromagnetic radiation of the same wavelength as the compound's maximum absorbance peaks, photodegradation of the compound can occur. Thus, it is an object of the present invention to provide a container that selectively blocks the wavelengths of light associated with melatonin's maximum absorbance peaks.

Figure 3:
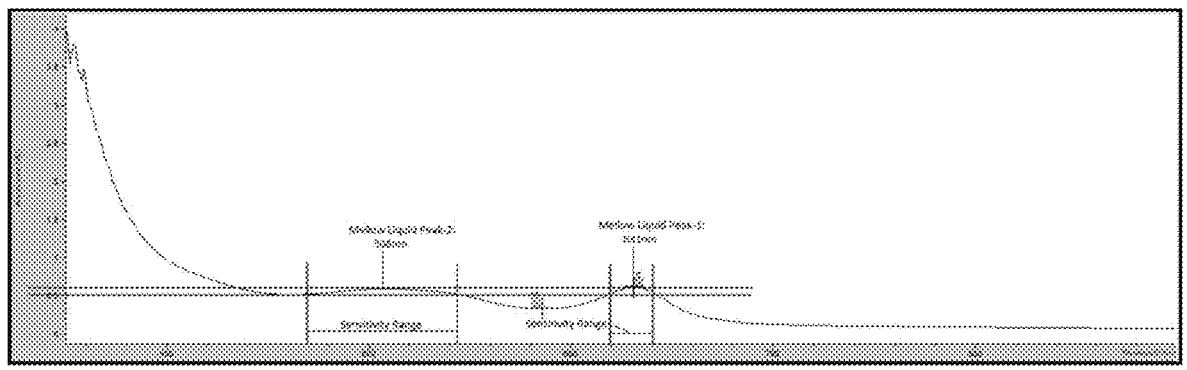
FIG. 3 shows the absorbance spectra of a composition comprising melatonin.

Current liquid melatonin compositions are often sold and/or stored in amber bottles. It was previously believed that providing an amber container for personal health compositions comprising melatonin would mitigate photodegradation. However, this strategy was based on the mistaken belief that melatonin was sensitive to ultraviolet radiation (UV). Amber bottles at least partially block the wavelengths of light associated with UV and some portions of the visible light spectrum associated with violet and blue light. Unexpectedly, it was found that melatonin's maximum absorbance peaks were not in the range of the light filtered by amber bottles. In FIG. 3, the ultraviolet-visible spectrum (UV-Vis) showed maximum absorbance peaks at 508 nm (green visible light) and 631 nm (red visible light). Without wishing to be bound by theory, it is believed that a container that can block light of wavelengths matching melatonin's maximum absorbance peaks can mitigate the photodegradation of personal health compositions comprising melatonin that typically occurs during storage of the personal health compositions. The present invention is thus based on the surprising discovery that a container that filters and/or blocks light with wavelengths of at least about 508 nm and/or about 631 nm can mitigate the photodegradation of personal health compositions comprising melatonin.

The foregoing summary is not intended to define every aspect of the invention, and additional aspects are described in other sections. In addition, the invention includes, as an additional aspect, all embodiments of the invention narrower in scope in any way than the variations defined by specific paragraphs set forth herein. For example, certain aspects of the invention that are described as a genus, and it should be understood that every member of a genus is, individually, an aspect of the invention. Also, aspects described as a genus or selecting a member of a genus should be understood to embrace combinations of two or more members of the genus. With respect to aspects of the invention described or claimed with "a" or "an," it should be understood that these terms mean "one or more" unless context unambiguously requires a more restricted meaning. The term "or" should be understood to encompass items in the alternative or together, unless context unambiguously requires otherwise. If aspects of the invention are described as "comprising" a feature, embodiments also are contemplated "consisting of" or "consisting essentially of" the feature.

Features of the compositions and methods are described below. Section headings are for convenience of reading and not intended to be limiting per se. The entire document is intended to be related as a unified disclosure, and it should be understood that all combinations of features described herein are contemplated, even if the combination of features are not found together in the same sentence, or paragraph, or section of this document. It will be understood that any feature of the methods or compounds described herein can be deleted, combined with, or substituted for, in whole or part, any other feature described herein.

As used herein, "translucent" is understood to describe a material that allows some electromagnetic radiation to pass through. A translucent material allows some light to pass through, such that some objects cannot be seen distinctly. Thus, a translucent material allows the consumer to see the material held within the translucent material, but in certain instances without much detail.

As used herein, "transparent" is understood to describe a material that allows nearly all electromagnetic radiation to pass through. A transparent material allows most of the light to pass through. Thus, a consumer will generally be able to see detailed images of other materials through transparent materials.

As used herein, "opaque" is understood to describe a material that does not allow nearly any light or electromagnetic radiation to pass through. Thus, a consumer will not generally be able to see materials through opaque materials.

As used herein, "electromagnetic radiation," describes all of the energies released into space by stars or the sun. Electromagnetic radiation includes energy in the forms of waves and/or photons. Electromagnetic radiation carries radiant energy. Electromagnetic radiation includes all electromagnetic radiation at every wavelength. Electromagnetic radiation includes, but is not limited to radio waves, microwaves, infrared radiation, visible light, ultraviolet radiation, x-ray, gamma rays, and/or mixtures thereof. Electromagnetic radiation can be provided by any source capable of producing electromagnetic radiation. Sources of electromagnetic radiation include, but are not limited to, a light emitting diode, incandescent bulb, a fluorescent bulb, a compact fluorescent bulb, a halogen bulb, a metal halide bulb, a high-pressure sodium bulb, a low-pressure sodium bulb, and/or a mercury vapor bulb. The electromagnetic radiation source can be a laser.

As used herein, "ultraviolet radiation," or "ultraviolet light" describe electromagnetic radiation from any source with a wavelength from about 10 nm to about 400 nm.

As used herein, "visible radiation," or "visible light" describe electromagnetic radiation from any source with a wavelength of from about 400 nm to about 750 nm.

As used herein, "UV-Vis light" describes electromagnetic radiation from any source with a wavelength of from about 190 nm to about 750 nm.

While compositions and methods are described herein in terms of "comprising" various components or steps, the compositions and methods can also "consist essentially of" or "consist of" the various components or steps, unless stated otherwise.

As used herein, the word "or" when used as a connector of two or more elements is meant to include the elements individually and in combination; for example, X or Y, means X or Y or both.

As used herein, a "preform" is understood to describe a precursor to a finished article. For example, for a blow molded article, the preform is the precursor article that is formed of the material that will be expanded or "blown" into the finished article. A preform is necessarily somewhat smaller than the finished blown article.

As used herein, the term "blow molding" as used herein is the process in which preforms are heated above their glass transition temperature, and then expanded in molds using a pressurized medium, preferably air, to form hollow articles, such as containers. Often, the preform is stretched with a stretch rod as part of the process.

Figure 1:
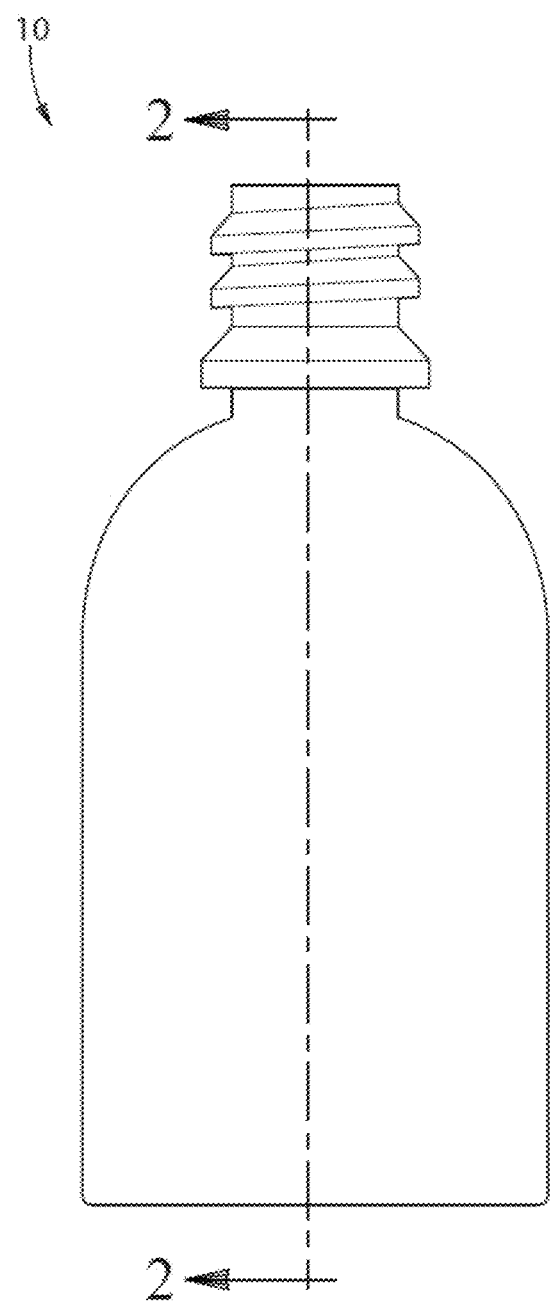
FIG. 1 is a perspective view of a container.
Figure 2:
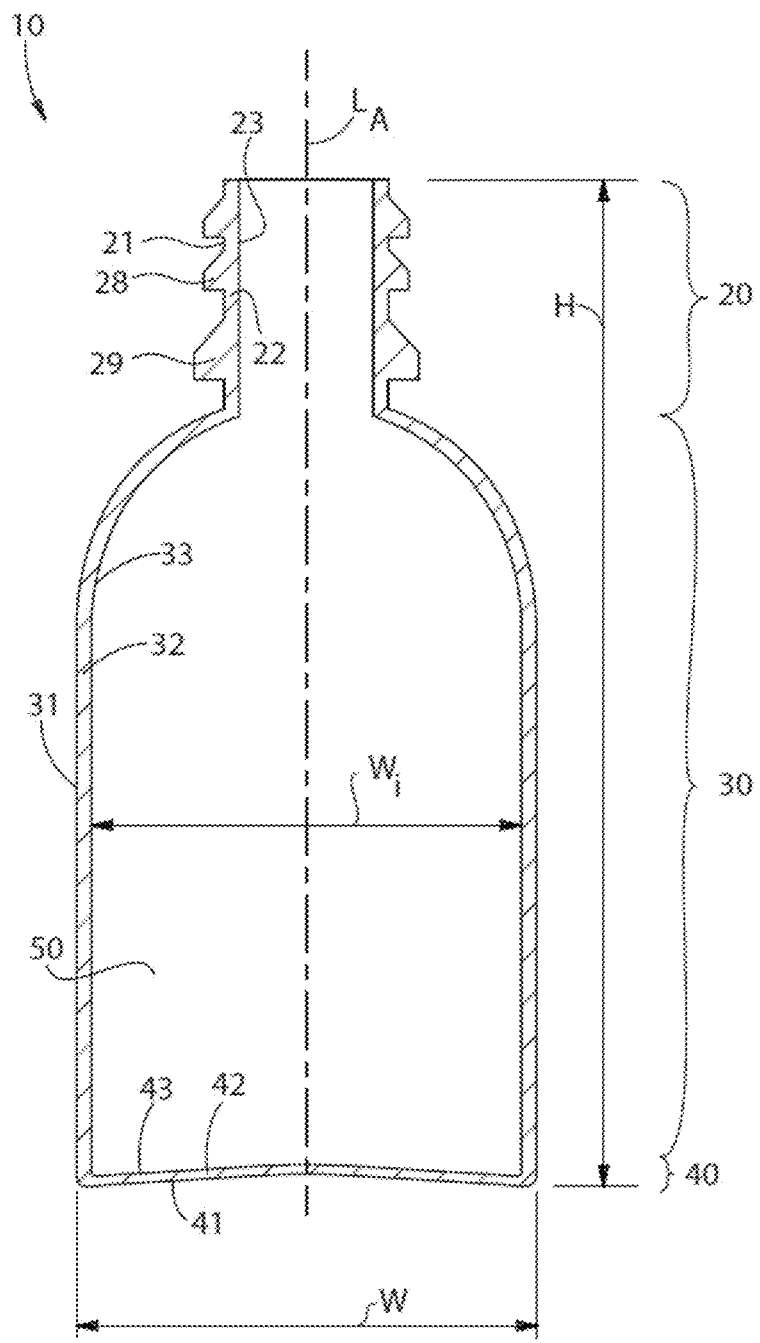
FIG. 2 shows a cross-sectional view of the container of FIG. 1 along section line 2.

As used herein, the "longitudinal" is the longitudinal axis (or centerline of the article, $L_A$), as in FIG. 2.

Several types of ranges are disclosed in the present invention. When a range of any type is disclosed or claimed, the intent is to disclose or claim individually each possible number that such a range could reasonably encompass, including end points of the range as well as any sub-ranges and combinations of sub-ranges encompassed therein.

The term "about" means that amounts, sizes, formulations, parameters, and other quantities and characteristics are not and need not be exact, but can be approximate and/or larger or smaller, as desired, reflecting tolerances, conversion factors, rounding off, measurement errors, and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about," the claims include equivalents to the quantities. The term "about" can mean within 10% of the reported numerical value, preferably within 5% of the reported numerical value.

The components of the present invention are described in the following paragraphs.

Container

The present invention is directed to a container for a personal health composition (or simply the "container"). The container (10) of the present invention can comprise a neck (20), a body (30), and a base (40). The neck (20), the body (30), and the base (40) can be created as a single, continuous article through any suitable manufacturing technique, such as, for example, injection molding, blow molding, additive manufacturing, and/or a combination of these techniques. The container (10) can be injection molded into a preform, which can then be blow molded into the finished container (10).

The container (10) can be any device capable of holding a liquid, semi-solid(s), and/or solid(s). The container (10) can be a squeeze container, a squeeze bottle, a bottle, a tottle, a vessel, a carafe, a flask, a jug, a jar, a can, a tube, a canteen, a canister, a carton, a cistern, a glass, a mug, and/or receptacle.

The container (10) can be made out of any material suitable for use as a container for a personal health composition. Non-limiting examples of suitable materials for the container (10) can include polyethylene terephthalate (PET), Glycol-modified Polyethylene Terephthalate (PETG), Oriented Polypropylene (OPP), Polyvinylchloride (PVC), Polyvinylidene Chloride (PVDC), Nylon, Polyethylene Terephthalate Polyester (PETP), Polyphene, and combinations thereof.

The container (10) can be made from any polyester. The formation of a polyester from an alcohol or a polyol and an acid or its ester encompasses many different suitable types of polyesters for use in this invention. The monomeric units can be formed reactions of either aliphatic moieties, aromatic moieties, or both.

Non-limiting examples of polyesters include terephthalates, terephthalate glycols, lactides, (hydroxy)alkanoates, copolyesters of terephthalic acid residues, 2,2,4,4-tetramethyl-1,3-cyclobutanediol, and 1,4-cyclohexanedimethanol, etc., or combinations thereof.

Additionally, one can use homopolyesters or copolyesters, such as homopolymers and copolymers of terephthalic acid and isophthalic acid. The linear polyesters may be produced by condensing one or more dicarboxylic acids or a lower alkyl diester thereof, e.g., dimethylterephthalate, terephthalic acid, isophthalic acid, phthalic acid, 2,5-, 2,6-, or 2,7-naphthalene dicarboxylic acid, succinic acid, sebacic acid, adipic acid, azelaic acid, bibenzoic acid and hexahydroterephthalic acid, or bis-p-carboxyphenoxyethane, with one or more glycols, e.g., ethylene glycol, pentyl glycol, and 1,4-cyclohexanedimethanol.

Of these various polyester candidates, because of commercial availability, the terephthalates, such as polyethylene terephthalate (PET) or polybutylene terephthalate (PBT), the lactides, such as polylactic acid (PLA), and the hydroxyalkanoates, such as polyhydroxybutyrate (PHB) or polyhydroxybutyrate-co-valerate (PHBV), are desirable for use. PET is currently preferred because of its ubiquity and cost, although PLA and PHBV are emerging as bio-derived thermoplastic polyesters which can supplant PET in whole or in part in certain markets.

The neck (20), the body (30), and the base (40) can be made out of the same material or different materials. The neck (20) of the container (10) can be associated with the body (30) of the container (10). The neck (20) of the container (10) can be a unitary piece, but may include separate non-structural elements, such as labels, grip structures, threads (28), a ledge (29) for the lid to rest on, etc., associated with the exterior surface (21) of the container (10). The neck (20) can comprise different regions of different materials, which are intrinsically bonded, chemically bonded, or otherwise associated with one another as a part of the manufacturing process.

The neck's (20) cross-sectional shape can be circular, rectangular, cylindrical, oval, triangular, polygonal, or any other desired shape. The neck's (20) cross-sectional shape can vary or be essentially consistent along the latitudinal axis ($L_A$), as shown in FIG. 2.

As shown in FIG. 2, the neck (20) can comprise a wall (22) of the neck (20). The wall (22) of the neck (20) can have an exterior surface (21) and an interior surface (23) and a thickness defined as the width between the exterior surface (21) and the interior surface (23). The neck (20) can be at least partially open or open, for example, such that the container (10) can be filled with a personal health composition.

As in FIG. 2, the body (30) of the container (10) can be associated with the neck (20) of the container (10) and the base (40) of the container (10). The body (30) of the container (10) can be a unitary piece, but may include separate non-structural elements, such as label panels, grip structures, etc. associated with the exterior surface (31) of the container (10). The body (30) can comprise different regions of different materials, which are intrinsically bonded, chemically bonded, or otherwise associated with one another as a part of the manufacturing process.

The body's (30) cross-sectional shape can be circular, rectangular, cylindrical, oval, triangular, polygonal, or any other desired shape. The body's (30) cross-sectional shape can vary or be essentially consistent along the latitudinal axis, as shown in FIG. 2.

As shown in FIG. 2, the body (30) can comprise a wall (32) of the body (30). The wall (32) of the body (30) can have an exterior surface (31), an interior surface (33), and a thickness defined as the width between the exterior surface (31) and the interior surface (33). The body (30) can be at least partially open or open, for example, such that the container (10) can be filled with a personal health composition.

As in FIG. 2, the base (40) of the container (10) can be associated with the body (30) of the container (10). The base (40) of the container (10) can be a unitary piece, but may include separate non-structural elements, such as label panels, grip structures, etc. associated with the exterior surface (41) of the container (10). The base (40) can comprise different regions of different materials, which are intrinsically bonded, chemically bonded, or otherwise associated with one another as a part of the manufacturing process.

The base's (40) cross-sectional shape can be circular, rectangular, cylindrical, oval, triangular, polygonal, or any other desired shape. The base's (40) cross-sectional shape can vary or be essentially consistent along the latitudinal axis, as shown in FIG. 2.

As shown in FIG. 2, the base (40) can comprise a wall (42) of the base (40). The wall (42) of the base (40) can have an exterior surface (41), an interior surface (43), and a thickness defined as the width between the exterior surface (41) and the interior surface (43). The base (40) can be at least partially closed or closed, for example, such that the container (10) can be filled with a personal health composition.

As shown in FIG. 2, the void created by the interior surface (23) of the neck (20), the interior surface (33) of the body (30), and the interior surface (43) of the base (40) can form the interior portion (50) of the container (10).

The average thickness of the wall (22) of the neck (20), the wall (32) of the body (30), and the wall (42) of the base (40) can be from about 0.001 inches to about 0.1 inches, from about 0.01 inches to about 0.05 inches, from about 0.02 inches to about 0.03 inches, at least about 0.01 inches, at least about 0.02 inches, less than about 0.04 inches, or less than about 0.03 inches. The average thickness of the wall (22) of the neck (20), the wall (32) of the body (30), and the wall (42) of the base (40) can be from about 0.1 mm to 10 mm, from about 0.5 mm to about 5 mm, from about 1 mm to about 5 mm, at least about 0.1 mm, at least about 1 mm, less than about 1 mm, or less than about 0.75 mm. The average thickness of the wall (22) of the neck (20), the wall (32) of the body (30), and the wall (42) of the base (40) can be equal or the values for the thicknesses can be different in each region.

The dimensions of the container (10) can be any suitable dimensions to provide the user with adequate supply of the personal health composition. For example, the total height, H, as shown in FIG. 2, of the container (10) can be from about 2 inches to about 20 inches, from about 3 inches to about 15 inches, or from about 4 inches to about 10 inches. The total height, as shown in FIG. 2, of the container (10) can be from about 50 mm to about 500 mm, from about 75 mm to about 300 mm, or from about 100 mm to about 250 mm. The total width, W, as shown in FIG. 2, of the preform (10) can be from about 1 mm to about 1 m, from about 5 mm to about 500 mm, from about 10 mm to about 300 mm, from about 10 mm to about 30 mm, or from about 10 mm to about 20 mm. The total width, $W_i$ as shown in FIG. 2, the interior portion (50) of the container (10) can be from about 1 mm to about 200 mm, from about 1 mm to about 100 mm, from about 10 mm to about 50 mm, or from about 15 mm to about 35 mm.

In one aspect, the container is opaque. In one aspect, the container is purple in color.

Colorant Composition

The container can comprise a colorant composition. The colorant composition can be within the wall (22) of the neck (20), the wall (32) of the body (30), and/or the wall (42) of the base (40). The colorant composition can be added to the material that makes up the walls (22, 32, and 42) of the container. Because light-sensitive therapeutics can absorb UV-Vis light in wavelengths in the broad range of 190 nm to 750 nm, the colorant composition comprises a combination of particular dye(s) and/or pigment(s) which collectively absorb, reflect, and block UV-Vis light in the same or similar wavelength range.

Unexpectedly, it has been found that three specific colorants, including two organic dyes of different chemistries and titanium dioxide pigment, provide the range of absorption sufficiently protective of light-sensitive therapeutics, such that their placement into polyester resin results in nearly total absorption of light in the wavelengths from 190 nm to 750 nm. Stated another way, the two organic dyes and pigments in the polyester resin in the plastic container minimize the transmission of light in the wavelengths from 190 nm to 750 nm before such UV-Vis light can reach the light-sensitive therapeutics and cause harmful photodegradation.

The first organic dye is an anthraquinone dyestuff which absorbs visible light at 430-630 nm. One commercially available dye is Macrolex™ Red Violet R Gran Solvent Soluble dye from Lanxess (Cologne, Germany). Generically using the Solvent Violet (SV) description, the first anthraquinone dyestuff is a combination of Disperse Violet 31 and Disperse Violet 26.

The second organic dye is also an anthraquinone dyestuff which absorbs visible light at 440-700 nm. One commercially available dye is Macrolex™ Violet B dye, also from Lanxess (Cologne, Germany). Generically using the SV description, the second anthraquinone dye is Solvent Violet 13.

The colorant composition can also comprise a pigment. The pigment can be within the wall (22) of the neck (20), the wall (32) of the body (30), and/or the wall (42) of the base (40). The pigment can be added to the polyester resin that makes up the walls (22, 32, and 42) of the container.

The pigment can be titanium dioxide which reflects visible light at 400 nm to 1000 nm and in suitable concentrations physically helps render opaque a plastic cross-section. One commercially available titanium dioxide is from Cristal (Tiona™ brand, Glen Burnie, Md.).

As the examples will demonstrate below, both dyes and titanium dioxide are required to provide chemical and physical minimization of transmission of light at 190 nm to 750 nm at 1% or less transmission in a plastic article with a thickness of 0.5 mm. As the examples will also demonstrate, very small quantities of such dyes and pigment are enough to combine to provide minimize light transmission at such wavelengths.

Optional Additives

The colorant composition of the present invention can include conventional plastics additives in an amount that is sufficient to obtain a desired processing or performance property for the compound. The amount should not be wasteful of the additive nor detrimental to the processing or performance of the compound. Those skilled in the art of thermoplastics compounding, without undue experimentation but with reference to such treatises as Plastics Additives Database (2004) from Plastics Design Library (www.williamandrew.com), can select from many different types of additives for inclusion into the compounds of the present invention.

Non-limiting examples of optional additives include adhesion promoters; biocides (antibacterials, fungicides, and mildewcides), anti-fogging agents; anti-oxidants; anti-static agents; bonding, blowing and foaming agents; dispersants; fillers and extenders; fire and flame retardants and smoke suppressants; impact modifiers; initiators; lubricants; micas; additional colorants; plasticizers; processing aids; release agents; silanes, titanates and zirconates; slip and anti-blocking agents; stabilizers; stearates; ultraviolet light absorbers; viscosity regulators; waxes; and combinations of them.

TABLE 1 shows acceptable, desirable, and preferable ranges of ingredients useful in the present invention, all expressed in weight percent (wt. %) of a masterbatch. The masterbatch can comprise, consist essentially of, or consist of these ingredients. Any number between the ends of the ranges is also contemplated as an end of a range, such that all possible combinations are contemplated within the possibilities of TABLE 1 as candidate masterbatches for use in this invention.

TABLE 1

Masterbatch components

| Ingredient (Wt. Percent) | Acceptable | Desirable | Preferable |
| --- | --- | --- | --- |
| Polyester Resin | 47-80.5 | 57.4-72.9 | 60.5-67.3 |
| First Anthraquinone Dye | 7-15 | 8-12 | 9.5-10.0 |
| Second Anthraquinone Dye | 2.5-4 | 3.1-3.6 | 3.2-3.5 |
| Titanium Dioxide | 10-24 | 15-20 | 18-20 |
| Optional Additives | 0-10 | 1-7 | 2-6 |

TABLE 2 shows the final compound ingredients computed at a 2% let down ratio ("LDR") in acceptable, desirable, and preferable ranges of ingredients useful in the present invention, all expressed in weight percent (wt. %) of a compound at the 2% LDR. The compound can comprise, consist essentially of, or consist of these ingredients. Any number between the ends of the ranges is also contemplated as an end of a range, such that all possible combinations are contemplated within the possibilities of TABLE 2 as candidate compounds, respectively, for use in this invention.

TABLE 2

Compound at Let Down Ratio of 2% (50:1 Ratio)

| Ingredient (Wt. Percent) | Acceptable | Desirable | Preferable |
|---|---|---|---|
| Polyester Resin | 98.94-99.61 | 99.15-99.46 | 99.21-99.35 |
| First Anthraquinone Dye | 0.14-0.30 | 0.16-0.24 | 0.19-0.20 |
| Second Anthraquinone Dye | 0.05-0.08 | 0.062-0.072 | 0.064-0.070 |
| Titanium Dioxide | 0.20-0.48 | 0.30-0.40 | 0.36-0.40 |
| Optional Additives | 0.00-0.20 | 0.02-0.14 | 0.04-0.12 |

The ratio of letdown determines the amount of polyester resin for the carrier of the concentrate and the amount of polyester resin into which the concentrate is let down. LDR from a masterbatch can range from about 0.5 to about 10% LDR, alternatively from about 1 to about 8% LDR, alternatively from about 1.25% to about 5% LDR, alternatively from about 2% to about 4% LDR. Preferably the LDR is about 2%. Moreover, a person having ordinary skill in the art without undue experimentation can adjust the LDR to accommodate preferences in the final plastic vessel to protect the light-sensitive therapeutics.

Processing

The preparation of masterbatches and compounds of the present invention is uncomplicated. Either one can be made in batch or continuous operations. Gravimetric blenders or feeders are recommended for better processing than dosing meters.

Mixing in a continuous process typically occurs in an extruder that is elevated to a temperature that is sufficient to melt the polymer matrix with addition either at the head of the extruder or downstream in the extruder of the liquid and solid ingredient additives. Extruder speeds can range from about 50 to about 1000 revolutions per minute (rpm), and preferably from about 300 to about 750 rpm. Typically, the output from the extruder is pelletized for later extrusion or molding into polymeric articles.

Mixing in a batch process typically occurs in a mixer that is also elevated to a temperature that is sufficient to melt the polymer matrix to permit addition of the solid ingredient additives. The mixing speeds range from 60 to 1000 rpm and temperature of mixing can be ambient. Also, the output from the mixer is chopped into smaller sizes for later extrusion or molding into polymeric articles.

Subsequent extrusion or molding techniques are well known to those skilled in the art of thermoplastics polymer engineering. Without undue experimentation but with such references as "Extrusion, The Definitive Processing Guide and Handbook"; "Handbook of Molded Part Shrinkage and Warpage"; "Specialized Molding Techniques"; "Rotational Molding Technology"; and "Handbook of Mold, Tool and Die Repair Welding", all published by Plastics Design Library (www.elsevier.com), one can make articles of any conceivable shape and appearance using compounds of the present invention.

Of the many types of plastic vessels, self-supporting plastic containers, such as plastic bottles of various sizes, is a preferred shape of the container for the transport and storage of light-sensitive therapeutics. Self-supporting containers are often made via stretch blow molding.

Stretch blow molding is a subset of conventional blow molding, often used in making containers. The final shape is achieved via one stage or two stages.

In a one stage blow molding, a "parison" is formed having some final dimensions (the "finish" such as the screw cap portion of the ultimate container) and nearly immediately then subjected to blow molding with a deliberate stretch of the non-final dimensions expanded to their intended shape. Depending on the design, the stretching occurs both in the axial direction of the parison and in the hoop or radial direction also.

In a two stage blow molding, a "preform" is formed via conventional injection molding and having some final dimensions (the "finish" such as the screw cap portion of the ultimate container) and the remainder having shrunken dimensions for convenience of transport and storage until final stress formation.

In the second stage, the preform is heated to an appropriate softening temperature and gas is used to deliberately stretch to its final intended shape. Depending on the design, the stretching occurs both in the axial direction of the preform and in the hoop or radial direction also.

The amount of deliberate stretching force applied, measured by the reduction in thickness in the preform to the final part can be described as the stretch ratio: wall thickness of preform divided by wall thickness of part.

The colorant composition can be molded into a final container while undergoing expansion at stretch ratios ranging from about 1.5:1 to about 200:1, and preferably from about 3:1 to about 50:1.

Also, the length of the preform usually expands during blow molding to a final part length about 1:1 to about 200:1. For the examples, which follow, that longitudinal or axial expansion ratio is about 2:1.

Heated air is usually used in the stretch blow molding process, although other gases can be used.

It is known that polyester can be strengthened by stretch blow molding because the resulting strain is hardened into the plastic article after cooling. This strengthening in a container can assist in the storage of fluids having a high vapor pressure, such as carbonated soft drinks and the like.

Personal Health Composition

The personal health composition comprises a photosensitive compound that undergoes photodegradation upon exposure to UV or visible light. The personal health composition can comprise melatonin, which can undergo photodegradation upon exposure to visible light. While it was initially thought that liquid melatonin was sensitive to UV light, it was unexpectedly found that liquid melatonin undergoes photodegradation upon exposure to visible light. Thus, amber bottles, which primarily filter UV light, are not effective at preventing the photodegradation of melatonin stored within.

The personal health composition can comprise from about 0.001% to about 99%, from about 0.001% to about 10%, from about 0.001% to about 1%, from about 0.001% to about 0.1%, from about 0.01% to about 0.02%, less than about 1%, or less than about 0.02%, by weight of the personal health composition of melatonin. In one aspect, the personal health composition comprising melatonin can be a liquid composition. In one aspect, the personal health composition can be an aqueous composition comprising melatonin. In one aspect, the personal health composition can be a solid dosage form comprising melatonin, such as a tablet, capsule, gummy, soft chew, or a chewable tablet.

The personal health composition can include other optional ingredients, such as sweeteners, solvents, buffers, preservatives, sensates, flavors, salivation agents, dyes, and/or a botanical blend.

The personal health composition can comprise one or more sweeteners to provide sweetness and taste masking of any ingredients that may be present. In one example, the composition comprises from about 2% to about 25% sweetener, in another example from about 5% to about 20% sweetener, in another example from about 7% to about 15% sweetener, and in another example from about 8% to about 12% sweetener. Non-limiting examples of sweeteners can include nutritive sweeteners, sugar alcohols, synthetic sugars, high intensity natural sweeteners, and combinations thereof.

Non-limiting examples of nutritive sweeteners can include glucose, sucrose, fructose, galactose, and combinations thereof.

Non-limiting examples of sugar alcohols can include xylitol, sorbitol, mannitol, maltitol, lactitol, isomalt, erythritol, glycerin, and combinations thereof. In one example, the composition can comprise from about 1% to about 30% sugar alcohol, in another example from about 5% to about 28% sugar alcohol, in another example about 10% to about 25% sugar alcohol, and in another example about 15% to about 23% sugar alcohol. In one example, the composition can comprise from about 5% to about 20% sorbitol, in another example from about 7% to about 18% sorbitol, and in another example from about 10% to about 15% sorbitol. In another example, the composition can comprise from about 3% to about 15% glycerin, in another example from about 5% to about 10% glycerin, and in another example from about 7% to about 9% glycerin.

Non-limiting examples of synthetic sweeteners can include sodium saccharin, acesulfame potassium, sucralose, aspartame, monoammonium glycyrrhizinate, neohesperidin dihydrochalcone, thaumatin, neotame, cyclamates, and mixtures thereof. In one example, the composition can comprise from about 0.01% to about 0.5% artificial sweetener, in another example from about 0.01% to about 0.3% artificial sweetener, and in another example about 0.05% to about 0.15% artificial sweetener.

Non-limiting examples of high intensity natural sweeteners can include neohesperidin dihydrochalcone, stevioside, rebaudioside A, rebaudioside C, dulcoside, monoammonium glycrrhizinate, thaumatin, and combinations thereof.

The personal health compositions typically comprise a solvent. A solvent can be used to dissolve the less soluble components into solution.

Non-limiting examples of solvents can include water, propylene glycol, ethanol, and mixtures thereof. In one example the composition comprises from about 60% to about 95% solvent, in another example from about 70% to about 90% solvent, and in another example from about 75% to about 85% solvent.

In one example, the composition comprises water and propylene glycol. In one example, the composition comprises from about 35% to about 95% water, in another example from about 40% to about 85% water, in another example from about 45% to about 80% water, in another example from about 68% to about 86% water. In another example, the composition can comprise from about 1% to about 10% propylene glycol, in another example from about 0.5% to about 5% propylene glycol, and in another example from about 1% to about 2% propylene glycol.

In one example, the composition can comprise a buffer. The buffer can help maintain a constant pH within the liquid composition. In one example, the liquid composition can comprise from about 0.05% to about 2% buffer, in another example from about 0.1% to about 1% buffer, in another example from about 0.15% to about 0.5% buffer, and in another example from about 0.18% to about 0.25% buffer. Buffers can include acetate buffers, citrate buffers, and phosphate buffers. Non-limiting examples of buffers can include acetic acid, sodium acetate, citric acid, sodium citrate, monobasic sodium phosphate, dibasic sodium phosphate, sodium carbonate, sodium bicarbonate, succinic acid, sodium succinate, potassium dihydrogen phosphate, phosphoric acid, and combinations thereof.

In one example, the composition can comprise a preservative. In one example, the liquid composition can comprise from about 0.01% to about 1% preservative, in another example from about 0.05% to about 0.5% preservative, in another example from about 0.07% to about 0.3% preservative, and in another example from about 0.08% to about 0.15% preservative. Non-limiting examples of preservatives can include benzalkonium chloride, ethylenediaminetetraacetic acid (EDTA), benzyl alcohol, potassium sorbate, parabens, benzoic acid, sodium benzoate, and mixtures thereof.

In one example, the composition can comprise a thickener. In one example, the liquid composition can comprise from 0.01% to 3% thickener, in another example 0.05% to 1.5% thickener, in another example 0.1% to 0.75% thickener, and in another example 0.12% to 0.3% thickener. Non-limiting examples of thickeners can include xanthan gum, carrageenan, polyacrylic acid, polyvinylpyrrolidone, cellulosic polymers including carboxymethycellulose, hydroxethylcellulose, hydroxymethylcellulose, and hydroxypropylmethylcellulose, and combinations thereof.

The liquid composition can optionally include one or more sensates. Non-limiting examples of sensates can include cooling sensates, warming sensates, tingling sensates, and combinations thereof. Sensates can be useful to deliver signals to the user.

Non-limiting examples of cooling sensates can include WS-23 (2-Isopropyl-N,2,3-trimethylbutyramide), WS-3 (N-Ethyl-p-menthane-3-carboxamide), WS-30 (1-glyceryl-p-mentane-3-carboxylate), WS-4 (ethyleneglycol-p-methane-3-carboxylate), WS-14 (N-t-butyl-p-menthane-3-carboxamide), WS-12 (N-(4-,ethoxyphenyl)-p-menthane-3-carboxamide), WS-5 (Ethyl-3-(p-menthane-3-carboxamido) acetate, Menthone glycerol ketal (sold as Frescolat® MGA by Haarmann & Reimer), (−)-Menthyl lactate (sold as Frescolat® ML by Haarmann & Reimer), (−)-Menthoxypropane-1,2-diol(sold as Coolant Agent 10 by Takasago International), 3-(1-menthoxy)propane-1,2-diol, 3-(1-Menthoxy)-2-methylpropane-1,2-diol, (−)-Isopulegol is sold under the name "Coolact P®" by Takasago International, cis & trans p-Menthane-3,8-diols(PMD38)—Takasago International, Questice® (menthyl pyrrolidone carboxylate), (1R, 3R,4S)-3-menthyl-3,6-dioxaheptanoate—Firmenich, (1R, 2S,5R)-3-menthyl methoxyacetate—Firmenich, (1R,2S, 5R)-3-menthyl 3,6,9-trioxadecanoate—Firmenich, (1R,2S, 5R)-menthyl 11-hydroxy-3,6,9-trioxaundecanoate—Firmenich, (1R,2S,5R)-3-menthyl (2-hydroxyethoxy) acetate—Firmenich, Cubebol—Firmenich, Icilin also known as AG-3-5, chemical name 1-[2-hydroxyphenyl]-4-[2-nitrophenyl-]-1,2,3,6-tetrahydropyrimidine-2-one), 4-methyl-3-(1-pyrrolidinyl)-2[5H]-furanone, Frescolat ML—menthyl lactate, Frescolat MGA—menthone glycerin acetal, Peppermint oil, L-Monomenthyl succinate, L-monomenthyl glutarate, 3-1-menthoxypropane-1,2-diol—(Coolact 10), 2-1-menthoxyethanol (Cooloact 5), TK10 Coolact (3-1-Menthoxy propane-1,2-diol), Evercool™ 180 (N-(4-cyanomethylphenyl)-p-menthanecarboxamide)), and combinations thereof. In one example, the composition can comprise from about 0.005% to about 1% cooling sensate, in another example from about 0.05% to about 0.5% cooling sensate, and in another example from about 0.01% to about 0.25% cooling sensate.

Additional non-limiting examples of flavoring ingredients can include peppermint oil, corn mint oil, spearmint oil, oil of wintergreen, clove bud oil, cassia, sage, parsley oil, marjoram, lemon, lime, orange, mango, cis-jasmone, 2,5-dimethyl-4-hydroxy-3(2H)-furanone, 5-ethyl-3-hydroxy-4-methyl-2(5H)-furanone, vanillin, ethyl vanillin, propenyl guaethol, heliotropine, 4-cis-heptenal, diacetyl, methyl-p-tert-butyl phenyl acetate, menthol, methyl salicylate, ethyl salicylate, 1-menthyl acetate, oxanone, alpha-irisone, methyl cinnamate, ethyl cinnamate, butyl cinnamate, ethyl butyrate, ethyl acetate, methyl anthranilate, iso-amyl acetate, iso-amyl butyrate, allyl caproate, eugenol, eucalyptol, thymol, cinnamic alcohol, octanol, octanal, decanol, decanal, phenylethyl alcohol, benzyl alcohol, alpha-terpineol, linalool, limonene, citral, maltol, ethyl maltol, carvone, menthone, β-damascenone, ionone, gamma decalactone, gamma nonalactone, gamma undecalactone and mixtures thereof. Generally suitable flavouring ingredients are those containing structural features and functional groups that are less prone to redox reactions. These include derivatives of flavouring ingredients that are saturated or contain stable aromatic rings or ester groups. In one example, the composition can comprise from about 0.01% to about 1% flavoring ingredients, in another example from about 0.05% to about 0.5% flavoring ingredients, and in another example from about 0.1% to about 0.3% flavoring ingredients.

The composition can optionally include one or more salivation agents. Non-limiting examples of salivation agents include formula (I):

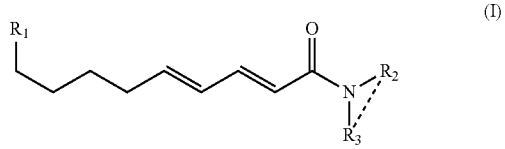

(I)

Wherein $R_1$ represents C1-C2 n-alkyl; $R_2$ is 2-methyl-1-propyl and $R_3$ is hydrogen, or $R_2$ and $R_3$ taken together is a moiety (designated by the dashed lines) having the formula—$(CH_2)_n$— wherein n is 4 or 5, and combinations thereof.

In an embodiment, the salivation agent comprises a material wherein $R_2$ is 2-methyl-1-propyl and $R_3$ is hydrogen, in another embodiment the salivating agent comprises a material wherein $R_1$ is C1 n-alkyl, $R_2$ is 2-methyl-1-propyl and $R_3$ is hydrogen. In another embodiment, the salivating agent comprises trans-pellitorin, a chemical having a structure according to formula (II):

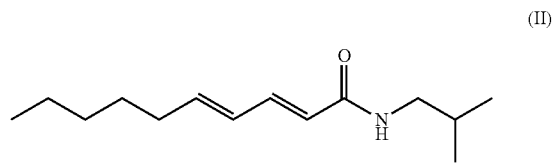 [SMILES: CCCCC/C=C/C=C/C(=O)NCC(C)C]

(II)

In another embodiment, the salivation agent can include sodium bicarbonate, sodium chloride, trans-pellitorin, and combinations thereof. In one example, salivation agents can be present from about 0.05% to about 2%, in another embodiment from about 0.1% to about 1%, and in another example from about 0.25%% to about 0.75%.

The composition can be any color. Non-limiting examples of colors can include red, green, amber, orange, yellow, blue, pink, violet, turquoise, and combinations thereof. In one example, the composition is purple. In another example, the liquid composition is clear.

The composition can also comprise a dye that provides the color. Non-limiting examples of dyes that may be used in the present invention include FD&C blue #1, FD&C blue #2, D&C blue #4, D&C blue #9, FD&C green #3, D&C green #5, D&C green #6, D&C green #8, D&C orange #4, D&C orange #5, D&C orange #10, D&C orange #11, FD&C red #3, FD&C red #4, D&C red #6, D&C red #7, D&C red #17, D&C red #21, D&C red #22, D&C red #27, D&C red #28, D&C red #30, D&C red #31, D&C red #33, D&C red #34, D&C red #36, D&C red #39, FD&C red #40, D&C violet #2, FD&C yellow #5, FD&C yellow #6, D&C yellow #7, Ext. D&C yellow #7, D&C yellow #8, D&C yellow #10, D&C yellow #11, and combinations thereof. In one example, the composition can comprise from about 0.001% to about 0.1% dye, in another example from about 0.002% to about 0.05% dye, and in another example form about 0.003% to about 0.01% dye.

The composition can comprise a botanical blend. The botanical blend can comprise one or more botanical components. The composition can comprise from about 0.001% to about 2%, from about 0.01% to about 1%, from about 0.1% to about 0.9%, less than about 1%, or less than about 0.75%, by weight of the composition, of the botanical blend. Non-limiting examples of botanical components that may be used in the present invention include the ginger Family (*Zigiberaceae*); licorice root (*Glycyrrhizin glabra*); marshmallow root (*Althea officinalis, Althea radix*); Chamomile (*Matricariae flos, Chamaemelum nobile*); Ashwaghandha (*Withania somnifera*); Fennel oil, Fennel Seed (*Foeniculum vulgare*); Caraway oil, Caraway seed (*Carum carvi, Carvi fructus, Carvi aetheroleum*); Lemon Balm (*Melissae folium, Melissa*); Horehound Herb (*Murrubii herba*); Flaxseed, flaxseed alpha-linoleic acid (*Lini semen*); Rosemary Leaf, rosemary extract (*Rosmarinus officinalis*, Rosemary folium); lavender (*Lavandula*); polyphenols, avocado extract comprising mannoheptulose, mannoheptulose (*Persea Americana*); valerian (*Valeriana officinalis*); grape seed extract; collagen; turmeric; and combinations thereof.

Product

Also described herein is a product comprising a container and a liquid composition, preferably a liquid personal health composition comprising melatonin. In one aspect, the container can comprise a polyester and a colorant composition, wherein the container can absorb, reflect, and/or block certain wavelengths of light. For example, the container can absorb, reflect, or block light in the range of from about 190 nm to about 750 nm, alternatively from about 190 nm to about 650 nm, alternatively from about 450 nm to about 650 nm, alternatively from about 450 to about 550 nm, alternatively from about 600 nm to about 650 nm, and/or combinations thereof. One of skill in the art would understand that the amount and/or proportion of the colorant composition within the container can be modified according to the desired thickness of the container (10). The light transmission can be determined through UV/Vis spectroscopy, as described herein.

In one aspect, the composition can be described by the percent loss of the photosensitive compound, preferably melatonin, after storage for a specified number of days at a specified set of light conditions. For example, the composition can have a percent loss of melatonin of about 30% or less, about 25% or less, about 15% or less, about 10% or less, from about 1% to about 30%, from about 1% to about 15%, or from about 5% to about 15%, by weight of the melatonin, after about 100 days, 200 days, 300 days, 1 year, or 5 years of storage under indoor or factory lighting conditions. The percent loss of melatonin can be determined by comparing the concentration of melatonin before and after treatment with light for a specified time to approximate the targeted number of exposure days to indoor and/or factory lighting as described herein.

EXAMPLES

Melatonin Absorbance

An absorbance spectrum was obtained of the melatonin sample of TABLE 6. 3 mL of the melatonin sample was placed in a 10 mm quartz cuvette and compared to a blank of distilled water. The Agilent Spectrophotometer (Model #8453, Agilent, Santa Clara, CA) was turned on 45 minutes prior to data acquisition to allow the lamps to warm up. The test range was 300 nm to 900 nm. The generated reading is shown in FIG. 3.

The melatonin sample displayed two maximum absorbance peaks in FIG. 3: at approximately 631 nm (primary peak) and at approximately 508 nm (secondary peak). Ranges of wavelengths of light that needed to be protected against (i.e. "Sensitivity Range") were the wavelengths of light within one tenth of the absorbance value at the maximum. The sensitivity range for the primary peak would be at least from about 620 nm to about 640 nm, as shown in FIG. 3. The sensitivity range for the secondary peak would be at least from about 470 nm to about 540 nm. Without wishing to be bound by theory, it is believed that when energy from electromagnetic radiation exceeds a compound's molecular bonding energy, photodegradation occurs. Additionally, when a compound is exposed to electromagnetic radiation of the same wavelength as the compound's maximum absorbance peaks and/or the sensitivity range(s), photodegradation of the compound can occur. Thus, it was an object of the present invention to provide a container that selectively blocks the wavelengths of light associated with at least the sensitivity ranges of the primary peak and/or the secondary peak illustrated in FIG. 3.

Container Absorbance

TABLE 3 shows the absorbance characteristics of containers with a variety of dyes or additives. The absorbance of the containers was determined using a Hunter UltraScan Color Spectrophotometer (Model # A41-1012-119, HunterLab, Inc., Reston, VA). First, the lamps for the spectrophotometer were allowed to warm up for about 45 minutes prior to generating any data. The spectrophotometer was placed in RSIN task mode. In order to standardize the RSIN task mode, a light trap (Serial # USP1851) was placed at the reflectance port of the spectrophotometer and was read by the spectrophotometer. Next, the white tile standard (Serial # EVU000904) was placed at the reflectance port and a sample was read by the spectrophotometer. The operating software then standardized the RSIN task mode.

Next, a calibration check was performed. A diagnostic green tile was placed at the reflectance port and read by the spectrophotometer. A XYZ color value was assigned by the operating software and compared to the originally calibrated XYZ color value displayed on the front of the instrument. If the values are within 0.3 units, the calibration check passes.

Finally, 3 inch×3 inch container pieces were cut out of the bottles and placed at the reflectance port. The test range was 350 nm to 800 nm. Values for the protection ranges for various containers were determined by evaluating the wavelengths of light TABLE 3 shows the absorbance ranges of the tested containers.

As shown in TABLE 3, none of the selected containers provided protection over both sensitivity ranges for melatonin as described above. As described above, the sensitivity ranges for liquid melatonin are at least from about 620 nm to about 640 nm and at least from about 470 nm to about 540 nm. The white opaque, translucent purple, and translucent blue containers were effective at protecting from wavelengths of 500-800 nm, 550-620 nm, and 530-630 nm, respectively. Thus, none of these bottles were effective at protecting against all of the wavelengths of light where liquid melatonin is sensitive. All of these bottles failed to protect below 500 nm.

The translucent amber, UV bottles and PET containers with UV inhibitors were effective at protecting from wavelengths of 360-560 nm, 337-380 nm, 330-380 nm, and 340-390 nm, respectively. Thus, none of these bottles were effective at protecting against all of the wavelengths of light where liquid melatonin is sensitive. All of these bottles failed to protect above 560 nm.

As described above, the sensitivity ranges for liquid melatonin are at least from about 620 nm to about 640 nm and at least from about 470 nm to about 540 nm. Since none of the tested containers could adequately protect across the entire sensitivity ranges for liquid melatonin, a new masterbatch was created.

TABLE 3

Protection Range of Materials with Various Dyes or Additives

| Container | TiO$_2$? | Protection Range |
| --- | --- | --- |
| White Opaque[a] | Yes | 500-800 nm |
| Translucent Purple[b] | No | 550-620 nm |
| Translucent Blue[c] | No | 530-630 nm |
| Translucent Amber[d] | No | 360-560 nm |
| 2 & 4% UV Bottles[e] | No | 337-380 nm |
| PET Container with UV Inhibitor[f] | No | 330-380 nm |
| PET Container with UV Inhibitor[g] | No | 340-390 nm |

[a]12 oz PET white at a 4% LDR, lot#122644 Axium, Mississauga, Ontario, Canada
[b]8 oz PET translucent purple at a 0.5% LDR using color CC102598092F, Axium, New Albany, OH
[c]Mucinex ® PET translucent blue, Reckitt Benckiser Group plc, Berkshire, England
[d]Amber Anti-UV Polybag, DispenserBag ™, Model no. MGUV3P0814
[e]Transluscent purple bottle with an ultraviolet light inhibitor (Ultimate UV 390) at a 2% and 4% LDR, lot #0618250, Axium, Mississauga, Ontario, CA
[f]PET container with PolyOne colorant CC010555277P2 with 0.09% Ultimate UV 390, PolyOne, Avon Lake, OH.
[g]PET container with PolyOne colorant CC010555277P2 with 0.12% Ultimate UV 390, PolyOne, Avon Lake, OH.

Container Absorbance

TABLE 4 shows the formulations of Comparative Examples A-B and Examples 1-2. Each of them was mixed in a high speed mixer at ambient temperature until all ingredients were well dispersed. Comparative Example A and Example 1 were masterbatches. Comparative Example B and Example 2 were compositions at a let down ratio of 2% of Comparative Example B and Example 1, respectively. Then the mixtures of each were melted and cast into a 0.5 mm thick plaque for testing of UV-Vis light transmission using a Perkin-Elmer UV-Visible spectrometer, following the instructions identified in the "Technical Note: Validating UV/Visible Spectrophotometers" published by Perkin-Elmer in 2012.

TABLE 5 shows the percentage light transmission values at various wavelengths for Comparative Example B and Example 2. While Comparative Example B provides nearly zero UV-Vis light transmissions from 190 nm to about 650 nm, the formulation failed to provide 1% or less light transmission starting between 650 nm and 700 nm and continuing up to 750 nm, the requirement for success. By contrast, Example 2 demonstrated 1% or less light transmission across the complete range of 190 nm-750 nm, satisfying requirements of UV-Vis protection for light-sensitive therapeutics.

Each of the amounts of the two dyes and the titanium dioxide pigment were doubled between Comparative Example B and Example 2 in order to achieve success. Opacity (physical light blockage) was contributed mostly by the titanium dioxide pigment which also contributed reflectance. Absorption was contributed mostly by the two dyes, at partially overlapping wavelengths.

It is unpredictable that the doubling of amount of the two anthraquinone dyes and titanium dioxide would turn failure into success, especially at 750 nm, where Example 2 outperforms Comparative Example B by a factor of seven times for the 0.5 mm thick samples. Indeed, Example 2 provides up to only 2.5% visible light transmission up to 850 nm.

It is also unpredictable and quite surprising that such a small increase of the amount of the two dyes and the one pigment (0.312 weight percent) in the compound of Example 2 vs. the compound of Comparative Example B would result in seven times less visible light transmission at 750 nm for the 0.5 mm thick samples.

Absorbance of Personal Health Compositions in Containers

TABLE 6 shows a non-limiting, example composition comprising melatonin that was placed in the containers of TABLE 7 to test their impact on the photodegradation of melatonin. TABLE 7 compares the effect of bottle type on the photodegradation of melatonin.

TABLE 4

Colorant Composition Formulations

| Ingredient (Wt. %) | Comp. A | Example 1 | Comp. B | Example 2 |
|---|---|---|---|---|
| Laser+ C (E60A) (Pulverized) polyethylene terephthalate copolymer resin (IV = 0.81) (DAK Americas) | 64.17 | 60.44 | 1.2834 | 1.209 |
| Laser+ C (E60A) (Pellet) polyethylene terephthalate copolymer resin (IV = 0.81) (DAK Americas) | 16.04 | 3.18 | 0.3208 | 0.0636 |
| Laser+ C (E60A) (Pellet) polyethylene terephthalate copolymer resin (IV = 0.81) (DAK Americas) | 0.0 | 0.0 | 98.0 | 98.0 |
| Macrolex Red Violet R Gran. Anthraquinone dye (Lanxess, Germany) -- Absorbs at 430-630 nm | 4.9 | 9.8 | 0.098 | 0.196 |
| Macrolex Violet B Anthraquinone dye (Lanxess, Germany) -- Absorbs at 440-700 nm. | 1.68 | 3.37 | 0.0338 | 0.0674 |
| Tiona 188 blue tone chloride-process rutile titanium dioxide pigment (Cristal) - Reflects at 400 nm-1000 nm | 9.0 | 18.0 | 0.18 | 0.36 |
| Irganox 1010 Pentaerythritol tetrakis(3-(3,5-DI-tert-butyl-4-hydroxyphenyl)propionate) phenolic anti-oxidant (BASF) | 0.2 | 0.2 | 0.004 | 0.004 |
| Epoxidized Soybean Oil plasticizer (Chemtura) | 1.0 | 0.0 | 0.02 | 0 |
| Maxsperse W-3000 alkoxylated alcohol dispersant (PCC Chemax) | 3.0 | 5.0 | 0.06 | 0.1 |

TABLE 5

Light transmission of Colorant Compositions
Light Transmission (%)

| Wavelength (nm) | Comp. B | Example 2 |
|---|---|---|
| 190-625 | ~0 | ~0 |
| 650 | 0.1 | ~0 |
| 700 | 2.5 | 0.2 |
| 750 | 7.0 | 1.0 |
| 800 | 12.0 | 1.5 |
| 850 | 20.0 | 2.5 |

TABLE 6

Personal Health Composition Example

| Component | (wt %) |
|---|---|
| Melatonin | 0.015 |
| Propylene Glycol | 1.500 |
| Sorbitol | 12.000 |
| Glycerin | 8.000 |
| Sodium Benzoate | 0.100 |
| Sodium Citrate | 0.204 |
| Citric Acid | 0.201 |
| Saccharin | 0.080 |
| Sucralose | 0.060 |
| Botanical Blend | 0.505 |
| Dye | 0.001 |

TABLE 6-continued

Personal Health Composition Example

| Component | (wt %) |
| --- | --- |
| Flavor | 0.295 |
| Water | Q.S. |

Compositions comprising melatonin were placed in the bottles shown in TABLE 7. Melatonin compositions were placed in a PET bottle wrapped in aluminum foil (Control, not introduced to light in anyway), two bottles comprising the colorant composition from Example 2 in TABLE 4 (Colorant Composition), and two bottles comprising titanium dioxide ($TiO_2$), but no other dyes (White Opaque from TABLE 3).

Bottles comprising an aqueous melatonin composition were placed in the chamber of an Atlas Suntest XLS (S/N 1011001, Mount Prospect, IL) and tested under ICH Q1B exposure parameters using a glass filter-set to block radiation outside of a 320-800 nm range. The glass filter-set that was used includes a Coated Quartz glass filter (Part #56055177, Mount Prospect, IL) and two Solar ID65 glass filters (Part #56079177, Mount Prospect, IL). The Atlas Suntest XLS can be used to check for property changes of materials and products due to sunlight, temperature, and/or moisture. The samples were exposed to a Xenon lamp (simulating factory/indoor lighting) with an intensity at 75 klux for 16 hrs to achieve 1200 klux·hrs, which is equivalent to 100 days of exposure to indoor and/or factory lighting.

The aqueous concentration of melatonin in the compositions was determined by Ultra Performance Liquid Chromatography (UPLC). A mobile phase A was prepared by adding 2.0 mL of Trifluoroacetic acid (Sigma Aldrich Co., St. Louis, MO, 99% purity) to a 2000 mL volumetric flask. The volumetric flask was filled with deionized water (MΩ2=18.2) until the meniscus of the deionized water was equal to the 2000 mL line. A mobile phase B was prepared by filtering and degassing HPLC grade acetonitrile (EMD Millipore Co., Burlington, MA, 99% purity). The diluent was prepared by combining mobile phase A with mobile phase B in a 75:25 volume ratio.

A melatonin stock solution was prepared by adding 40.00 mg of melatonin to a 200 mL volumetric flask. The volumetric flask was filled with the prepared diluent until the meniscus of the diluent was equal to the 200 mL line to create the 200 μg/mL stock solution. Four more calibration standards were prepared by diluting 5 mL, 25 mL, 50 mL, and 75 mL of the stock solution with 95 mL, 75 mL, 50 mL, and 25 mL of the diluent to create calibration standards of 10 μg/mL, 50 μg/mL, 100 μg/mL, and 150 μg/mL respectively.

A calibration curve was calculated by running the five calibration standards on a Waters Acquity UPLC (G15SDI954G, Milford, MA) that includes a Waters Acquity Detector (Part # G15UPL549A, Milford, Mass.) and Pump (Part # F15QSM016A, Milford, MA). The prepared mobile phase A and mobile phase B were used as the mobile phase with a flow rate of 0.400 mL/min. The samples were placed in an HPLC auto-sampler vial (Part #46610-724, VWR International, Radnor, PA) for analysis. The injection volume was 1 μL at 40.0° C. The column used was a Waters Acquity UPLC BEH C18, 130 A, 1.7 μm, 2.1×150 mm (Part #186002353, Milford, MA). Under these UPLC conditions, the peak for melatonin appeared at approximately 2.3 minutes at the UV detection wavelength of 278 nm. The area under each melatonin curve was plotted with its known concentrations to create a calibration curve, from which a concentration can be calculated from a sample with an unknown concentration of melatonin.

Using the developed calibration curve, the concentration of melatonin was determined for samples immediately prior to placement in the Atlas Suntest XLS in various bottles and after 16 hours in the Atlas Suntest XLS, which approximated 100 days under normal factory lighting. A value for % Loss of Melatonin could be determined by comparing the calculated melatonin concentration values before and after the test.

TABLE 7 displays the % Loss of Melatonin for a variety of different bottles. The white opaque bottle displayed an average % Loss of Melatonin values of 46.8%, which indicated that after 100 days, nearly half of amount of melatonin will undergo photodegradation while in an opaque bottle without any dye. In contrast, the bottles with the colorant composition (which included two anthraquinone dyes and $TiO_2$) displayed an average % Loss of Melatonin values of 13.0% after 16 hours, which indicated that after 100 days, much less melatonin will undergo photodegradation while in a bottle with the colorant composition. Thus, a container with the colorant composition comprising a first anthraquinone dye, a second anthraquinone dye, and titanium dioxide will outperform a container comprising only titanium dioxide.

TABLE 7

Loss of Melatonin in Various Containers

| Sample Name | % Loss of Melatonin | Hours |
| --- | --- | --- |
| Control | N/A | 0 |
| Colorant Composition | 13.0* | 16 |
| White Opaque | 46.8* | 16 |

*Average of two replicate runs

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A product comprising:
   (a) a container, wherein the container is a bottle that mitigates photodegradation of melatonin by selectively filtering or blocking light at wavelengths selected from about 470 nm to about 540 nm and from about 620 nm to about 640 nm, the container comprising:
      (i) from about 98.94% to about 99.61%, by weight of the container, of a polyester;
      (ii) a colorant composition comprising:
         (1) from about 0.14% to about 0.30%, by weight of the container, of a first anthraquinone dye,
         (2) from about 0.05% to about 0.08%, by weight of the container, of a second anthraquinone dye, and
         (3) from about 0.20% to about 0.48%, by weight of the container, of titanium dioxide; and
   (b) a liquid composition comprising melatonin.

2. The product of claim 1, wherein the liquid composition is an aqueous composition comprising melatonin.

3. The product of claim 1, wherein the container absorbs, reflects, and blocks light in the range of about 190 nm to about 750 nm with 1% or less light transmission at a container thickness of 0.5 mm.

4. The product of claim 3, wherein the container absorbs, reflects, and blocks light in the range of about 450 nm to about 650 nm with 1% or less light transmission at a container thickness of 0.5 mm.

5. The product of claim 1, wherein the liquid composition has a percent loss of melatonin of about 30% or less, by weight of initialmelatonin, after 100 days of exposure to factory or indoor light levels.

6. The product of claim 1, wherein the liquid composition has a percent loss of melatonin of about 15% or less, by weight of initial melatonin, after 100 days of exposure to factory or indoor light levels.

7. The product of claim 1, wherein the container is formed by blow molding.

8. The product of claim 1, wherein the container has a body wall with a thickness of from about 0.1 mm to about 10 mm.

9. The product of claim 1, wherein the liquid composition further comprises a botanical blend.

10. The product of claim 1, wherein the container comprises the colorant composition at a let down ratio (LDR) of about 2% from masterbatch.

* * * * *